United States Patent [19]

Tamborski

[11] 4,081,473
[45] Mar. 28, 1978

[54] FLUOROALKYLENEETHER DIFUNCTIONAL COMPOUNDS

[75] Inventor: Christ Tamborski, Dayton, Ohio

[73] Assignee: The United States of America as represented by the Secretary of the Air Force, Washington, D.C.

[21] Appl. No.: 737,120

[22] Filed: Oct. 29, 1976

Related U.S. Application Data

[62] Division of Ser. No. 610,520, Sep. 4, 1975, Pat. No. 4,011,255.

[51] Int. Cl.$^2$ ............................................. C07C 119/00
[52] U.S. Cl. ............................................. 260/453 RW
[58] Field of Search ................................. 260/453 RW

[56] References Cited

U.S. PATENT DOCUMENTS

| | | | |
|---|---|---|---|
| 3,523,132 | 8/1970 | Dorfman et al. | 260/453 RW |
| 3,532,725 | 10/1970 | Dorfman et al. | 260/465.4 |
| 3,535,351 | 10/1970 | Dorfman et al. | 260/465.4 |
| 3,557,165 | 1/1971 | Dorfman et al. | 260/465.4 |
| 3,846,376 | 11/1974 | Evers | 260/47 R |
| 3,903,166 | 9/1975 | Evers | 260/47 R |
| 3,994,861 | 11/1976 | Evers | 260/61 |
| 4,005,142 | 1/1977 | Evers | 260/47 R |

Primary Examiner—Joseph Paul Brust
Assistant Examiner—Molly C. Eakin
Attorney, Agent, or Firm—Joseph E. Rusz; Cedric H. Kuhn

[57] ABSTRACT

Omega-carbomethoxyperfluoroalkylene ether iodides are reacted with metallic zinc to yield alpha-omega perfluoroalkyleneether diesters. The diesters are reacted with ammonia to form diamides, the diamides are reacted with phosphorus pentoxide to form dinitriles, and the dinitriles are esterified with methanol to form diimidate esters. The diimidate esters are particularly useful as monomers in synthesizing perfluoroalkylene ether bibenzoxazole polymers possessing thermooxidative stability and outstanding low temperature viscoelastic properties.

5 Claims, No Drawings

FLUOROALKYLENEETHER DIFUNCTIONAL COMPOUNDS

RIGHTS OF THE GOVERNMENT

The invention described herein may be manufactured and used by or for the Government of the United States for all governmental purposes without the payment of any royalty.

This is a division of application Ser. No. 610,520 filed Sept. 4, 1975, and now issued as U.S. Pat. No. 4,011,255.

FIELD OF THE INVENTION

This invention relates to fluoroalkyleneether difunctional compounds. In one aspect it relates to alpha-omega perfluoroalkyleneether diimidate esters. In another aspect it relates to a process for preparing the diimidate esters.

BACKGROUND OF THE INVENTION

There is a requirement for thermally stable, elastomers for various aerospace seal and sealant applications. To be suitable for such applications, the polymeric materials must retain their elastomeric properties at subzero temperatures. Furthermore, the polymers should possess other desirable properties such as hydrolytic stability and fuel resistance. In U.S. Pat. No. 3,846,376, R. C. Evers discloses polymers that go a long way toward fulfilling the aforementioned requirement. A bisaminophenol compound is condensed with a diimidate ester in preparing polymers having a glass transition temperature (Tg) of about $-20°$ C. The Tg of a polymer is an indication of the temperature at which it retains its elastomeric properties. There is still a need for polymers having even lower glass transition temperatures for extremely low temperature applications.

It is an object of this invention, therefore, to provide monomers that are particularly suitable for use in preparing thermally stable polymers having low glass transition temperatures.

Another object of the invention is to provide novel fluoroalkyleneether difunctional compounds.

A further object of the invention is to provide a process for preparing the fluoroalkyleneether difunctional compounds.

Other objects and advantages of the invention will become apparent to those skilled in the art upon consideration of the accompanying disclosure.

SUMMARY OF THE INVENTION

The present invention resides in fluoroalkyleneether difunctional compounds having the following formula:

$$X-R_f-X$$

wherein each X is $CH_3OC(O)$, $C_2H_5OC(O)$, $H_2N(CO)$, CN or $(HN=)COCH_3$ and wherein $R_f$ is $(CF_2)_4O(CF_2)_4O(CF_2)_4$ or $Y[CF(CF_3)CF_2O]_n(CF_2)_4[OCF_2CF(CF_3)]_nY$, where each Y is $(CF_2)_4O$ or $CF(CF_3)OCF_2CF_2O$ and n is an integer from 1 to 5, inclusive. The diesters [X is $CH_3OC(O)$, or $C_2H_5OC(O)$] are intermediates in preparing the diamides [X is $H_2N(CO)$] while the diamides are intermediates in synthesizing the dinitriles (X is CN). Finally, the dinitriles are intermediates in preparing the diimidate esters [X is $(HN=)COCH_3$]. The preferred compounds of this invention, i.e., the diimidate esters, have the following formula:

$$CH_3O(NH)C-R_f-C(NH)OCH_3,$$

where $R_f$ is as indicated above.

In preparing the diimidate esters of this invention, a four-step procedure is followed as shown by the following representative equations:

$$CH_3OC(O)(CF_2)_4O[CF(CF_3)CF_2O]_2CF_2CF_2I + Zn$$
$$\rightarrow [CH_3OC(O)(CF_2)_4O[CF(CF_3)CF_2O]_2CF_2CF_2]_2 \quad (I)$$

$$[CH_3OC(O)(CF_2)_4O[CF(CF_3)CF_2O]_2CF_2CF_2]_2 + NH_3 \rightarrow$$
$$[NH_2C(O)(CF_2)_4O[CF(CF_3)CF_2O]_2CF_2CF_2]_2 \quad (II)$$

$$[NH_2C(O)(CF_2)_4O[CF(CF_3)CF_2O]_2CF_2CF_2]_2 +$$
$$P_2O_5 \rightarrow [NC(CF_2)_4O[CF(CF_3)CF_2O]_2CF_2CF_2]_2 \quad (III)$$

$$[NC(CF_2)_4O[CF(CF_3)CF_2O]_2CF_2CF_2]_2 + CH_3OH \rightarrow$$
$$[NH=C(OCH_3)(CF_2)_4O[CF(CF_3)CF_2O]_2CF_2CF_2]_2 \quad (IV)$$

As seen from equation I, in the first step an omega-carbomethoxyperfluoroalkylene oxide iodide is reacted with particulate zinc metal to form a diester. An omega-carboethoxyperfluoroalkylene oxide iodide can also be used in the reaction. The reaction is carried out in acetic anhydride and 1,1,2-trifluorotrichloroethane under reflux conditions and in an inert atmosphere. In the second step (equation II), ammonia is bubbled through an ether-1,1,2-trifluorotrichloroethane solution of the diester recovered from the first step to form a diamide product. The diamide product recovered from the second step is mixed and heated with phosphorus pentoxide in the third step (equation III) to provide the dinitrile. In the final and fourth step (equation IV), the dinitrile recovered from the third step is added to a solution of sodium in methanol. In the reaction that occurs, the diimidate ester is formed.

In addition to the iodoester shown in equation I, iodoesters having the following formulas are employed as starting materials in synthesizing the compounds of this invention:

$$C_2H_5OC(O)(CF_2)_4OCF_2CF_2I;$$

$$CH_3OC(O)(CF_2)_4O[CF(CF_3)CF_2O]_3CF_2CF_2I; \text{ and}$$

$$CH_3OC(O)CF(CF_3)OCF_2CF_2OCF(CF_3)CF_2OCF_2CF_2I.$$

In preparing the iodoesters, an anhydrous alkali metal fluoride, such as potassium fluoride, and an omega-carbomethoxyperfluoroalkyleneether acid fluoride are first mixed in tetraglyme solvent. After stirring the mixture at ambient temperature or about 0.5 to 3 hours, the mixture is cooled and a molar excess of iodine monochloride is added. Thereafter, the reactor containing the materials is pressured with tetrafluoroethylene until there is substantially no pressure drop. The reaction mixture is then poured into water. After removing any excess iodine by a sodium thiosulfate wash, the reaction mixture is extracted with a fluorinated solvent. The iodoester is thereafter separated from the extracted reaction mixture by fractional distillation. Examples of acid fluorides used in preparing the iodoesters have the following formula:

$$C_2H_5OC(O)(CF_2)_3COF;$$

$$CH_3OC(O)(CF_2)_4OCF(CF_3)CF_2OCF(CF_3)COF;$$

CH$_3$OC(O)(CF$_2$)$_4$[CF(CF$_3$)CF$_2$O]$_2$CF(CF$_3$)COF;

and

FCOCF(CF$_3$)OCF$_2$CF$_2$OCF(CF$_3$)COF.

The acid fluorides can be prepared by following essentially the procedure described by C. G. Fritz et al in U.S. Pat. No. 3,114,778. For example, a substituted perfluoroalkylether acid fluoride, CH$_3$OC(O)(CF$_2$)$_3$-COF, is reacted with hexafluoropropylene epoxide in the presence of a metal fluoride, such as potassium fluoride, to yield oligomeric products having the following formula:

CF$_3$OC(O)(CF$_2$)$_4$O[CF(CF$_3$)CF$_2$O]$_n$CF(CF$_3$)COF.

The oligomeric products can be separated by fractional distillation to provide a series of omega-carbomethoxyperfluoroalkyleneether acid fluorides in which $n$ can vary from zero to 10. Also, according to the disclosure of C. G. Fritz et al, a perfluoroacyldianion ($^\theta$CF$_2$R$_f$CF$_2$O$^\theta$) is reacted with hexafluoropropylene epoxide in the presence of a metal halide to yield a perfluoroalkyleneether bis acid fluoride having the following formula:

FCOCF(CF$_3$)OCF$_2$R$_f$CF$_2$OCF(CF$_3$)COF.

For a more complete description of the preparation of the iodoesters, reference may be made to application Ser. No. 610,471 of common assignee, filed on Sept. 4, 1975, by C. Tamborski and T. Psarras, the disclosure of which is incorporated herein by reference.

The diimidate esters of this invention are useful as monomers in preparing thermally stable polymers. Thus, polycondensation of the diimidate esters with fluorocarbon ether bis(o-aminophenol) monomers provide linear fluorocarbon ether bibenzoxazole polymers. The polymers are elastomeric, have a very low glass transition temperature, and are oxidatively stable at elevated temperatures. The polycondensation reaction is usually conducted in hexafluoroisopropanol at about 50 to 55° C in the presence of four molar equivalents of glacial acetic acid. Examples of fluorocarbon ether bis(o-aminophenol) monomers include 1,11-bis(3-amino-4-hydroxyphenyl)-perfluoro-3,9-(dioxaundecane; 1,14-bis(3-amino-4-hydroxyphenyl)-perfluoro-5,10-dimethyl-3,6,9,12-tetraoxatetradecane and 1,17-bis(3-amino-4-hydroxyphenyl)perfluoro-3,6,9,14-tetraoxaheptadecane. For a description of the preparation of these monomers, reference may be had to U.S. Pat. No. 3,846,376 and to application Ser. No. 610,470, of common assignee, filed on Sept. 4, 1975 by R. C. Evers, both of which are incorporated herein by reference.

A more comprehensive understanding of the invention can be obtained by referring to the following illustrative examples which are not intended, however, to be unduly limitative of the invention.

EXAMPLE I

(1) Synthesis of diethylperfluoro-6,11-dioxahexadecanediote

ICF$_2$CF$_2$O(CF$_2$)$_4$CO$_2$C$_2$H$_5$ + ZN →
C$_2$H$_5$O$_2$C(CF$_2$)$_4$O(CF$_2$)$_4$O(CF$_2$)$_4$CO$_2$C$_2$H$_5$

A mixture of the iodoester ICF$_2$CF$_2$O(CF$_2$)$_4$-CO$_2$C$_2$H$_5$ (30.4 g, 0.059 mole), 40 mesh zinc (12.0 g, 0.184 mole), acetic anhydride (36.0 g, 0.353 mole) and 1,1,2-trichlorotrifluoroethane (90 ml) were heated under a nitrogen atmosphere to reflux temperature (ca. 54° C) with stirring for a period of 24 hours. During this time a white precipitate formed. The reaction mixture was cooled, filtered and the filtrate was hydrolyzed. The organic layer that formed was separated, dried and distilled under reduced pressure. The diester product distilled at 110°–113° C. at 0.5 mm (86.5% yield). The $^1$H and $^{19}$F nuclear magnetic resonance data and infrared data were consistent with the product's chemical structure. Mass spectral analysis, calculated M$^+$778 found M$^+$778 and elemental analysis were consistent with the proposed structure.

Analysis - Calc'd: C,27.78; H,1.30 Found: C,27.55; H,1.20

(2) Synthesis of perfluoro-6,11-dioxahexadecanediamide

C$_2$H$_5$O$_2$C(CF$_2$)$_4$O(CF$_2$)$_4$O(CF$_2$)$_4$CO$_2$C$_2$H$_5$ + NH$_3$ →
NH$_2$(O)C(CF$_2$)$_4$O(CF$_2$)$_4$O(CF$_2$)$_4$C(O)NH$_2$ +
2C$_2$H$_5$OH

An excess of ammonia was bubbled through an ether-1,1,2-trichlorotrifluoroethane solution (200 ml) of diethylperfluoro-6,11-dioxahexadecanedioate (19.6 g, 0.025 mole). The solvents were removed from the reaction leaving a white solid which on repeated washing with 1,1,2-trichlorotrifluoroethane yielded 17.7 g of the diamide product, m.p. 157°–158° C. Infrared and nuclear magnetic resonance, $^1$H and $^{19}$F analysis were consistent with the diamide structure. Mass spectral analysis, calculated, M$^+$720, found M$^+$720 and elemental analysis were consistent with the diamide structure.

Analysis - Calc'd: C,23.35; H,0.56; N,3.89 Found: C,23.30; H,0.38; N,3.89

(3) Synthesis of perfluoro-6,11-dioxahexadecanedinitrile

NH$_2$(O)C(CF$_2$)$_4$O(CF$_2$)$_4$O(CF$_2$)$_4$C(O)NH$_2$ + P$_2$O$_5$ →
NC(CF$_2$)$_4$O(CF$_2$)$_4$O(CF$_2$)$_4$CN + H$_3$PO$_4$

The perfluoro-6,11-dioxahexadecanediamide (16.6 g, 0.023 mole) was mixed with an excess of phosphorus pentoxide, placed in a distillation flask and heated to 210° C for 2 hours. The reaction mixture was cooled, a vacuum of 105 mm was applied and heat was reapplied. The fraction boiling between 120°–125° C at 105 mm was collected (15.3 g, 96% yield). Analysis of the product confirmed the dinitrile structure. Infrared and nuclear magnetic resonance $^1$H and $^{19}$F were consistent with the structure. Mass spectral analysis, calculated M$^+$684, found M$^+$684 and elemental analysis were consistent with the proposed dinitrile structure.

Analysis - Clac'd: C,24.58; H,0.0; N,4.09 Found: C, 24.85; H,0.00; N,4.20

(4) Synthesis of dimethylperfluoro-6,11-dioxahexanediimidate

NC(CF$_2$)$_4$O(CF$_2$)$_4$O(CF$_2$)$_4$CN + 2CH$_3$OH →
CH$_3$O(NH)C(CF$_2$)$_4$O(CF$_2$)$_4$O(CF$_2$)$_4$C(NH)OCH$_3$

Approximately 0.1 gram of sodium was dissolved in anhydrous methanol (50 ml). To this solution was added the perfluoro-6,11-dioxahexadecanedinitrile (13.0 g, 0.019 mole). The reaction was stirred at room temperature for approximately 18 hours. On adding water to the methanol solution, a heavy lower organic layer was formed, phase separated, dried and distilled. The product distilled at 99°–100° C at 0.42 mm (78% yield). The infrared data and nuclear magnetic resonance $^1$H and $^{19}$F were consistent with the diimidate structure. Mass spectral analysis, calculated M$^+$748, found M$^+$748 and elemental analysis were consistent with the proposed diimidate structure.

Analysis - Calc'd: C,25.68; H,1.08; N,3.74 Found: C,25.72; H,1.12; N,3.73

EXAMPLE II

A series of experiments identified in the table below as A, B and C was carried out in which diesters, diamides, dinitriles and diimidate esters of this invention were prepared in accordance with the procedure described in Example I. The iodoesters used as the starting materials in the indicated series of experiments were as follows:

$$CH_3OC(O)(CF_2)_4O[CFCF_3CF_2O]_2CF_2CF_2I \quad (A)$$

$$CH_3OC(O)(CF_2)_4[CF(CF_3)CF_2O]_3CF_2CF_2I \quad (B)$$

$$CH_3OC(O)CF(CF_3)OCF_2CF_2OCF(CF_3)CF_2O\\CF_2CF_2I \quad (C)$$

The products obtained in each series of experiments runs corresponded to the formula X—R$_f$—X, where X is as shown in the table and R$_f$ is shown in footnotes to the table.

The data obtained in the experiments are set forth in the table.

(3) $R_f = CF(CF_3)OCF_2CF_2OCF(CF_3)CF_2O(CF_2)_4OCF_2CF(CF_3)OCF_2CF_2OCF(CF_3)$ (4) Amides characterized by infrared analysis.

(5) Molecular weight by mass spectral analysis.

As seen from the foregoing, the present invention provides fluoroalkyleneether difunctional compounds containing ester, amide, nitrile and imidate ester groups. The diimidate esters are particularly useful as monomers in synthesizing perfluoroalkyleneether bibenzoxazole polymers possessing thermooxidative stability and outstanding low temperature viscoelastic properties. These polymer properties render them especially useful in seal and sealant applications.

As will be evident to those skilled in the art, various modifications of the invention can be made without departing from the spirit and scope of the invention.

I claim:

1. A fluoroalkylether difunctional compound having the following formula:

$$CH_3O(NH)C-R_f-C(NH)OCH_3,$$

wherein R$_f$ is $(CF_2)_4O(CF_2)_4O(CF_2)_4$ or $Y[CF(CF_3)CF_2O]_n(CF_2)_4[OCF_2CF(CF_3)]_nY$, where each Y is $(CF_2)_4O-$ or $CF(CF_3)OCF_2CF_2O-$, and n is an integer from 1 to 5, inclusive.

2. The compound according to claim 1 in which R$_f$ is $(CF_2)_4O(CF_2)_4O(CF_2)_4$.

3. The compound according to claim 1 in which R$_f$ is $Y[CF(CF_3)CF_2O]_n(CF_2)_4[OCF_2CF(CF_3)]_nY$, where n is an integer from 1 to 5, inclusive.

4. The compound according to claim 3 in which Y is $(CF_2)_4O-$.

5. The compound according to claim 3 in which Y is $CF(CF_3)OCF_2CF_2O-$.

TABLE

| R$_f$ | X—R$_f$—X | Yield, (%) | B.P.° C/mm | M.W. (5) Calc'd / Found | C Calc'd / Found | N Calc'd / Found | N Calc'd / Found |
|---|---|---|---|---|---|---|---|
| A$^{(1)}$ | CH$_3$OC(O) | 68 | 126°/0.008 | 1414 / 1395 (M-F) | 23.8 / 23.3 | 0.43 / 0.41 | — |
| | H$_2$N(CO)$^{(4)}$ | 98 | | | | | |
| | CN | 71 | 123°/0.10 | 1348 / 1329 (M-F) | 23.1 / 22.9 | — | 2.07 / 2.20 |
| | (HN=)COCH$_3$ | 86 | 136°/0.02 | 1412 / 1412 | 23.8 / 24.2 | 0.57 / 0.65 | 1.98 / 1.98 |
| B$^{(2)}$ | CH$_3$OC(O) | 51 | 197°/0.24 | 1746 / 1727 (M-F) | 23.4 / 23.7 | 0.35 / 0.27 | — |
| | H$_2$N(CO)$^{(4)}$ | 85 | | | | | |
| | CN | 61 | 158°/0.18 | 1680 / 1661 (M-F) | 22.9 / 22.9 | — | 1.67 / 1.67 |
| | (HN=)COCH$_3$ | 75 | 204°/0.95 | 1744 / 1743 (M-H) | 23.4 / 23.5 | 0.46 / 0.41 | 1.61 / 1.49 |
| C$^{(3)}$ | CH$_3$OC(O) | 81 | 118°/0.12 | 1114 / 1095 (M-F) | 23.7 / 23.8 | 0.54 / 0.95 | — |
| | H$_2$N(CO)$^{(4)}$ | 93 | | | | | |
| | CN | 72 | 156°/45 | 1048 / 1029 (M-F) | 22.9 / 22.7 | — | 2.67 / 2.73 |
| | (HN=)COCH$_3$ | 64 | 105°/0.19 | 112 / 112 | 23.8 / 23.7 | 0.72 / 0.90 | 2.52 / 2.51 |

(1) $R_f = (CF_2)_4O[CF(CF_3)CF_2O]_2(CF_2)_4[OCF_2CF(CF_3)]_2O(CF_2)_4$ (2) $R_f = (CF_2)_4O[CF(CF_3)CF_2O]_3(CF_2)_4[OCF_2CF(CF_3)]_3O(CF_2)_4$